United States Patent [19]

Pilipski

[11] 4,318,710
[45] Mar. 9, 1982

[54] CONVERSION OF CELLULOSE INTO CHARCOAL

[75] Inventor: Mark Pilipski, 89 Mountainside Ter., Clifton, N.J. 07013

[73] Assignees: Martin F. Sturman, Melrose Park, Pa.; Michael Ebert, Mamaroneck, N.Y.; Mark Pilipski, Clifton, N.J.

[21] Appl. No.: 108,057

[22] Filed: Dec. 28, 1979

Related U.S. Application Data

[63] Continuation-in-part of Ser. No. 62,980, Aug. 2, 1979, Pat. No. 4,260,685.

[51] Int. Cl.$^3$ ............................ C10L 5/40; C10L 5/02
[52] U.S. Cl. ....................................... 44/1 F; 44/10 C; 252/444; 423/449
[58] Field of Search ............ 44/1 R, 1 F, 10 C, 10 K; 252/444, 445; 423/449

[56] References Cited

U.S. PATENT DOCUMENTS

| | | | |
|---|---|---|---|
| 148,778 | 3/1874 | Tait | 423/449 |
| 2,977,325 | 3/1961 | Feustel et al. | 252/445 |
| 3,436,312 | 4/1969 | Leonor | 44/1 R |
| 3,557,020 | 1/1971 | Shindo et al. | 252/445 X |
| 3,832,306 | 8/1974 | Hackett et al. | 423/449 X |
| 3,960,768 | 6/1976 | Ripperger et al. | 423/449 X |
| 3,998,756 | 12/1976 | Sutherland | 423/449 X |
| 4,149,995 | 4/1979 | Murty | 252/444 |

FOREIGN PATENT DOCUMENTS

411918 6/1934 United Kingdom ................ 252/445

*Primary Examiner*—Carl F. Dees
*Attorney, Agent, or Firm*—Michael Ebert

[57] ABSTRACT

A process for converting wood stock or other cellulosic material into charcoal, use being made for this purpose of liquid anhydrous hydrogen chloride at ambient temperatures.

7 Claims, No Drawings

CONVERSION OF CELLULOSE INTO CHARCOAL

RELATED APPLICATION

This application is a continuation-in-part of my copending application Ser. No. 062,980, filed Aug. 2, 1979 now U.S. Pat. No. 4,260,685, entitled "Saccharification of Cellulose," whose entire disclosure is incorporated herein by reference.

BACKGROUND OF INVENTION

This invention relates generally to a process for producing charcoal, and in particular to a technique wherein cellulosic stock is converted, without combustion, into charcoal by means of a catalytic agent.

Charcoal is a substance composed almost entirely of carbon, hydrogen, oxygen, this product being usually obtained by burning organic material in the absence of air by a destructive distillation technique. Because of its physical and chemical properties, charcoal yields a greater amount of heat in proportion to its volume than is obtainable from a corresponding quantity of wood. Moreover, as a fuel, it has the further advantage of being virtually smokeless.

Charcoal has a wide range of applications; for not only is it a valuable fuel, but it has metallurgical, chemical and various other practical uses. For economic reasons, the use of charcoal in metallurgy has given way to coke, but it remains an important material for the chemical industry. In its activated form it is useful as an adsorptive agent for the purification of gas and liquids.

In my above-identified copending application, cellulosic stock from any available source is subjected to hydrolysis by a liquid anhydrous chloride agent and converted thereby into glucose and other reducing substances. The glucose is then fermented to produce ethanol or ethyl alcohol, a valuable fuel as well as a solvent. In the present invention, the same agent or an agent having analogous chemical characteristics is used to effect conversion of cellulose into charcoal which is usable as a fuel or for any other known purpose.

Because billions of tons of carbon are fixed every year on the land area of the earth by photosynthesis, out of which about half appears in the form of cellulose, the ability to convert cellulose into almost pure carbon (i.e. charcoal) at low cost, affords a potential source of fuel of extraordinary magnitude. The fact that petroleum-derived hydrocarbon fuels are becoming increasingly scarce and much more expensive lends particular significance to this alternative source of fuel. Moreover, this source, which is derived from wood and other organic matter, is renewable and therefore effectively inexhaustible.

SUMMARY OF INVENTION

The main object of this invention is to provide a technique which entails no burning to convert cellulosic material into charcoal.

A significant feature of the invention is that the charcoal produced thereby has greater caloric value for a given amount of starting stock than that produced by conventional techniques.

More particularly, it is an object of this invention to provide a process for converting wood stock and any biomass having a significant cellulosic content into charcoal, conversion being effected at ambient temperatures by means of a catalyst constituted by liquid anhydrous hydrogen chloride or an agent having analogous chemical characteristics.

Also an object of this invention is to provide an efficient and economic technique of the above type which makes use of an agent which is not consumed in the reaction and which may be reconstituted and recycled.

DESCRIPTION OF INVENTION

I have found that by maintaining cellulosic stock such as pine sawdust, mechanical fiber, Kraft fiber or newspapers in a bath of liquid anhydrous hydrogen chloride beyond the time required for saccharification thereof, the wood is converted to a charcoal. As disclosed in my above-identified copending application, a woody substrate, when reacted for minutes in liquid anhydrous hydrogen chloride, yields sugars. I have discovered that this same woody substrate when kept in the bath of liquid anhydrous hydrogen chloride for several hours is converted to charcoal.

My tests show that when wood sawdust is exposed to liquid anhydrous hydrogen chloride it is converted into charcoal in less than 8 hours. On the other hand, the same amount of wood sawdust when exposed to gaseous anhydrous hydrogen chloride is also converted to charcoal; but in this instance, the completion of the conversion process takes more than a month. In both cases (using liquid or gaseous anhydrous hydrogen chloride) charcoal is produced at ambient temperatures.

I believe the relative rapidity of the reaction in liquid anhydrous hydrogen chloride as against the very slow conversion process when using gaseous anhydrous hydrogen chloride is due to the high density of this agent in the liquid state and its low density in the gaseous state. At slightly elevated temperatures, the reaction of cellulosic material with liquid anhydrous hydrogen chloride may be accelerated.

The introduction of cellulosic stock, such as pine sawdust, to liquid anhydrous hydrogen chloride gives rise to heat. I believe this exothermic reaction is due to the extraction and mixing of any small amount of water present within the cellulosic stock with the anhydrous hydrogen chloride. Any such water is immediately consumed by the hydrolytic saccharification of cellulose. After this initial heat is generated, the reaction appears to proceed without giving up any heat or requiring any measurable amounts of heat, as in an endothermic reaction.

After the charcoal has been formed, the hydrogen chloride must be purged from the charcoal. For this step, a dry stream of nitrogen is used to extract the hydrogen chloride from the produced charcoal. The purged hydrogen chloride is then recondensed for recycling. In practice, as an alternative to nitrogen any dry non-reactive gas or non-reactive fluid may be used to wash any residual hydrogen chloride from the charcoal. Thus hydrogen chloride is not consumed by the conversion process, and it is reclaimable.

I tested for residual chlorine compounds within the produced charcoal. Using KITAGAWA ® tubes and also a modified Fujiware test for this purpose, it was determined that less than 1 ppm of halogenated hydrocarbons was present in the charcoal. (This was the limit of detectability for these tests.)

In my test procedures, I tested for the presence of bromine, chlorine, chloroform, chlorobenzene, 1,2-dichloroethylene, ethylene chloride, hydrogen chloride, methyl bromide, methyl chloride, nitrogen dioxide, perchloroethylene, trichloroethylene, and vinyl chloride. I also sampled air drawn through the charcoal as well as effluent gases produced by heating the charcoal and also by burning the charcoal. I found no chlorine or chlorine compounds present in this charcoal or in its effluent gases. In summary, these tests indicated that there is no residual hydrogen chloride and no chlorinated hydrocarbons were present in charcoal produced by the action of anhydrous chloride upon cellulosic stock.

I also tested the charcoal produced by my process for the presence of chloride ions and found that those chloride ions present were matched in milliequivalents/liter to an almost equal amount of sodium ions, thereby indicating that any trace metals (sodium, magnesium, potassium, etc.) normally found in wood had been converted to chloride salts of these metals.

The charcoal produced by the action of anhydrous hydrogen chloride upon wood is soft and easily ground to a fine powder. This charcoal can be ground, packed, caked, or briquetted for ease of transportation. The produced charcoal occupies much less volume than the starting cellulosic stock, but its density is two to three times greater than the starting wood stock.

The caloric value of the charcoal produced by my process is equivalent to starting wood stock, which represents a distinct advantage over traditionally-produced charcoal. Before the 1900's, charcoal was the primary fuel for industrial processes. Charcoal was supplanted by coal and coke because the then-prevailing economic factors favored coal mining instead of the kiln-production of charcoal. Because the density of various coals is higher than the density of wood and charcoal, more coal can be shipped using fewer containers than are required to ship an equal weight of wood.

The traditional method for producing charcoal (destructive distillation) requires that wood be heated in an enclosed container or kiln whereby approximately one-half to two-thirds of the original fuel is gasified. As a consequence, usually more than half the original calories present in the wood stock are sacrificed in the traditional production of charcoal. Therefore, if one begins with one ton (2,000 lbs.) of wood and uses destructive distillation to manufacture charcoal, only 400–600 lbs. of charcoal are obtained. This charcoal would have a density of about twice that of the original wood. Some of the lost weight may be recovered by condensing many of the volatile hydrocarbons in the manner disclosed in the text, *Forest Energy and Economic Development* (D. E. Earl)—Clarendon Press, Oxford 1975 (page 34) during the early phases of destructive distillation. The fuel capacity of charcoal in terms of BTU/lb. produced by destructive distillation is about twice the value of the original wood stock.

By way of example, if we start with one ton of wood with a fuel capacity of approximately 5,700 BTU/lb., we would derive by destructive distillation 500 lbs. of charcoal with a fuel capacity of about 11,500 BTU/lb. Thus with the conventional destructive distillation technique, one starts with a potential 11.4 million BTU's and ends up with a potential 5.75 million BTU's. Hence in the traditional production of charcoal, nearly half of the potential fuel is destroyed.

Using my process (anhydrous hydrogen chloride), I have found that the BTU/lb. of the product charcoal is equivalent to the BTU/lb. of the original wood, as evidenced by the following results for four samples obtained when using the ASTM procedure D-2015.

PURPOSE

To determine the gross heat of combustion of the submitted samples.

PROCEDURE

Tests were conducted in accordance with ASTM procedure D-2015. At the client's request, no sulfur correction was made.

RESULTS

| Identification | Gross Heat of Combustion |
| --- | --- |
| Pine Sawdust | 11,778 BTU/lb. |
| Pine Sawdust post reaction | 11,756 BTU/lb. |
| Mechanical Fibre | 12,453 BTU/lb. |
| Mechanical Fibre post reaction | 13,518 BUT/lb. |

In short, my process changes the physical characteristics of the wood stock (for example, its density), but does not forfeit any of its potential fuel capacity.

The utilization of a modern fuel such as coke (which in essence is a charcoal-like substance produced from coal or oil) entails a technology that is completely compatible with the utilization of wood charcoal as a fuel. Therefore, no major redesign of furnaces is required to use charcoal as a fuel. Charcoal has an added advantage over coal or coke; this advantage being charcoal's low sulfur content. Indeed, charcoal when it is burned gives off virtually no sulfur compounds, no phosphorus compounds, or nitrogen oxides, the pollutants normally yielded by coal.

The above-identified pending application derives ethanol from cellulosic stock by first saccharifying the stock. If we convert only some of the original cellulosic stock to glucose and on to ethanol and further convert any remaining cellulose (not converted to glucose) to charcoal to provide the fuel required to effect distillation of the ethanol, ample fuel for such a procedure is present within the original cellulosic stock.

Roughly, if we start with a ton of wood stock (at $\approx$ 10,000 BTU/lb) and convert some percentage of that wood to glucose, say, 10%, and the remainder to charcoal, we can ferment the 200 lbs. of glucose into alcohol (150 lbs.). Distillation of this much ethanol requires, ideally, 60,000 BTU's. The alcohol produced would represent approximately 2,000,000 BTU's. The charcoal produced by the action of anhydrous hydrogen chloride would represent approximately 18,000,000 BTU's; thus more than enough to use for the distillation of the ethanol.

The process in accordance with the invention (using hydrogen chloride) to produce charcoal can also be used to carbonize many toxic wastes which now pose a health problem and are difficult to dispose. My process would be economically attractive because high pyrolysis temperatures are not required.

Other compounds besides hydrogen chloride will work for this process. Obviously, the other hydrogen halides will function as hydrogen chloride in this respect. It is believed that boron trichloride and boron trifluoride will also function as catalysts for my process. Lithium chloride, in a molten state (this may be used to carbonize toxic organic wastes) will also function in the above described manner. I believe that chlorides having chlorine present with a valence of minus 1 ($-1$) will also function as catalysts; i.e.:

mecury chloride, HgCl
copper chloride, CuCl
boron trichloride, $BCl_3$
aluminum trichloride, $AlCl_3$
zinc chloride, $ZnCl_2$
cadmium chloride, $CdCl_2$
gallium chloride, $GaCl_3$
silicon chloride, $SiCl_4$
silver chloride, AgCl
gold chloride, AuCl

I claim:

1. A technique for converting raw stock that is rich in cellulose to charcoal having a high caloric value, comprising the steps of:

A. subjecting the stock to an anhydrous liquid hydrogen halide at about ambient temperature for a time period extending beyond that necessary to hydrolyze the cellulose and sufficient to convert the stock into charcoal; and B. purging the hydrogen halide from the resultant charcoal.

2. A technique as set forth in claim 1, wherein the stock before being subjected to the liquid is first formed into particles to promote the reaction.

3. A technique as set forth in claim 1 wherein the anhydrous liquid hydrogen halide is hydrogen chloride.

4. A technique as set forth in claim 1 wherein said purging is effected by means of a non-reactive fluid to extract any residual hydrogen halide from the charcoal.

5. A technique as set forth in claim 4 wherein said fluid is constituted by a dry stream of nitrogen.

6. A technique as set forth in claim 1, further including the step of recondensing the purged hydrogen halide and recycling the liquid in the process.

7. A technique as set forth in claim 1 further including the step of briquetting the charcoal for ease of transportation.

* * * * *